(12) United States Patent
Fitzli et al.

(10) Patent No.: US 9,171,484 B2
(45) Date of Patent: Oct. 27, 2015

(54) DETERMINING LOCATION AND ORIENTATION OF AN OBJECT POSITIONED ON A SURFACE

(75) Inventors: Peter Andreas Maspoli Fitzli, Washington, DC (US); J. Michael Brown, Washington, DC (US); Robert F. Cohen, Kensington, MD (US); Robert Falk, Takoma Park, MD (US); Tianning Xu, Duluth, GA (US)

(73) Assignee: Immersion Corporation, San Jose, CA (US)

( * ) Notice: Subject to any disclaimer, the term of this patent is extended or adjusted under 35 U.S.C. 154(b) by 2350 days.

(21) Appl. No.: 12/043,236

(22) Filed: Mar. 6, 2008

(65) Prior Publication Data

US 2009/0225024 A1    Sep. 10, 2009

(51) Int. Cl.
    *G06F 3/03*   (2006.01)
    *G09B 23/28*  (2006.01)
    *G06T 7/00*   (2006.01)
    *A61B 17/00*  (2006.01)

(52) U.S. Cl.
    CPC ............ *G09B 23/285* (2013.01); *G06F 3/0317* (2013.01); *G06T 7/0044* (2013.01); *A61B 2017/00707* (2013.01); *G06T 2207/30004* (2013.01)

(58) Field of Classification Search
    CPC ....... G06F 3/03; G06F 3/0304; G06F 3/0317; G09B 23/285
    See application file for complete search history.

(56) References Cited

U.S. PATENT DOCUMENTS

| 4,961,138 A | 10/1990 | Gorniak |
| 4,980,871 A | 12/1990 | Sieber et al. |

(Continued)

FOREIGN PATENT DOCUMENTS

| DE | 10258952 | 8/2004 |
| GB | 2 419 664 A | 5/2006 |

(Continued)

OTHER PUBLICATIONS

Van Sickle, K.R. et al., "Construct validation of the ProMIS simulator using a novel laparoscopic suturing task," Surgical Endoscopy and Other Interventional Techniques, Official Journal of the Society of American Gastrointestinal and Endoscopic Surgeons (SAGES) and European Associate for Endoscopic Surgery (EAES), Springer-Verlag, NE, vol. 19, No. 9, Sep. 1, 2005, pp. 1227-1231.

(Continued)

*Primary Examiner* — Ilana Spar
(74) *Attorney, Agent, or Firm* — Kilpatrick Townsend & Stockton LLP (57) ABSTRACT

Systems and methods are described in the present disclosure for determining the location and orientation of an object placed on a surface. One such system, among others, includes an optical device physically supported by an object at a fixed position with respect to a reference point of the object. The system also includes a surface upon which the object can be placed. A reference pattern, which is applied to the surface, includes an array of markings visible to the optical device. The array of markings includes encoded location information and orientation information. In addition, the system includes a processing device in communication with the optical device. The processing device is configured to calculate the location and orientation of the reference point of the object with respect to the surface.

24 Claims, 7 Drawing Sheets

(56) References Cited

U.S. PATENT DOCUMENTS

| | | | |
|---|---|---|---|
| 5,088,046 | A | 2/1992 | McMurtry |
| 5,181,181 | A | 1/1993 | Glynn |
| 5,273,038 | A | 12/1993 | Beavin |
| 5,296,846 | A | 3/1994 | Ledley |
| 5,482,472 | A | 1/1996 | Garoni et al. |
| 5,546,943 | A | 8/1996 | Gould |
| 5,609,485 | A | 3/1997 | Bergman et al. |
| 5,661,506 | A | 8/1997 | Lazzouni et al. |
| 5,724,264 | A | 3/1998 | Rosenberg et al. |
| 5,769,640 | A | 6/1998 | Jacobus et al. |
| 5,882,206 | A | 3/1999 | Gillio |
| 5,956,040 | A | 9/1999 | Asano et al. |
| 5,971,767 | A | 10/1999 | Kaufman et al. |
| 6,193,519 | B1 | 2/2001 | Eggert et al. |
| 6,210,168 | B1 | 4/2001 | Aiget et al. |
| 6,623,433 | B2 | 9/2003 | Webler et al. |
| 6,703,570 | B1 | 3/2004 | Russell et al. |
| 6,726,638 | B2 | 4/2004 | Ombrellaro |
| 6,758,676 | B2 | 7/2004 | Eggert et al. |
| 7,835,892 | B2 | 11/2010 | Butsev et al. |
| 2002/0168618 | A1 | 11/2002 | Anderson et al. |
| 2004/0009459 | A1 | 1/2004 | Anderson et al. |
| 2005/0271302 | A1 | 12/2005 | Khamene et al. |
| 2006/0064007 | A1 | 3/2006 | Comaniciu et al. |
| 2006/0184013 | A1 | 8/2006 | Emanuel et al. |
| 2007/0275359 | A1 | 11/2007 | Rotnes et al. |

FOREIGN PATENT DOCUMENTS

| | | |
|---|---|---|
| JP | H04-332544 | 11/1992 |
| JP | H07-171154 | 7/1995 |
| JP | 2002-336247 | 11/2002 |
| JP | 2003-061956 | 3/2003 |
| JP | 2003-067784 | 3/2003 |
| JP | 2003-319939 | 11/2003 |
| JP | 2004-070669 | 3/2004 |
| JP | 2004-070670 | 3/2004 |
| JP | 2004-159781 | 6/2004 |
| JP | 2004-171251 | 6/2004 |
| WO | WO 99/38141 | 7/1999 |
| WO | WO 01/71643 A1 | 9/2001 |
| WO | WO 02/094080 | 11/2002 |
| WO | WO 03/001358 A1 | 1/2003 |
| WO | WO 03/096307 A1 | 11/2003 |
| WO | WO 2006/104440 A1 | 10/2006 |

OTHER PUBLICATIONS

About the Logitech io2 Paper, http://www.logitech.com/index.cfm/66/456&cl=us,en.

Polhemus Liberty Electromagnetic Motion Tracking System, http://www.polhemus.com/index_print.php?page=Motion_Liberty.

Ascension Products—Flock of Birds, http://www.ascension-tech.com/products/flockofbirds.php.

Hexamite Ultrasound, http://www.hexamite.com.

HiBall-3100™ Wide-Area, High-Precision Tracker and 3D Digitizer, http://www.3rdtech.com/HiBall.htm.

Wacom Components:Technology:EMR® Technology, http://wwww.wacom-components.com/english/technology/emr.html.

Mentice—Medical Simulators, http://www.mentice.com/templates/ment01.asp?sida=31.

Bates, Lisa M. et al., "A Method for Ultrasound Image Based Correction of Intraoperative Brain Shift," Proc. SPIE Medical Imaqinq 2000; Image Display and Visualization 3976: pp. 58-68.

Bro-Nielsen, Morten, "Finite Element Modeling in Surgery Simulation," Proceedings of the IEEE, vol. 86, No. 3, Mar. 1998, pp. 490-503.

Chen, Hongsheng et al., "Fast Voxelization of Three-Dimensional Synthetic Objects," Journal of Graphics Tools, vol. 3, No. 4, 1998, pp. 33-45.

Freidlin Raisa Z. et al., "NIHmagic: 3D Visualization, Registration and Segmentation Tool," $28^{th}$ AIPR Workshop: 3D Visualization for Data Exploration and Decision Making, Proc. of SPIE vol. 3905, 2000, pp. 8 pages.

Hesina, Gerd et al., "Distributed Open Inventor: A Practical Approach to Distributed 3D Graphics," Vienna University of Technology, Austria, 1999, pp. 74-81.

Iwata, Hiroo et al., "Volume Haptization", Institute of Engineering Mechanics, 1993, pp. 16-23.

Kreeger, Kevin et al., "Mixing Translucent Polygons with Volumes," Dept. of Computer Science, SUNY at Stony Brook, 1999, pp. 191-199.

Minsky, Margaret et al., "Feeling and Seeing: Issues in Force Display," Dept. of Computer Science, 1990, pp. 235-242, 270.

Stanley, Michael C. et al., "Computer Simulation of Interacting Dynamic Mechanical Systems Using Distributed Memory Parallel Processors," DSC-vol. 42, Advances in Robotics, ASME 1992, pp. 55-61.

Su, S. Augustine et al., "The Virtual Panel Architecture: A 3D Gesture Framework," Computer Science Department, 1993, pp. 387-393.

Weiler, Manfred et al., "Direct Volume Rendering in OpenSG," Computers & Graphics 28,2004, pp. 93-98.

Weiskopf, Daniel et al., "Volume Clipping via Per-Fragment Operations in Texture-Based Volume Visualization," Visualization and Interactive Systems Group, 2002, pp. 93-100.

Westermann, Rudiger et al., "Efficiently Using Graphics Hardware in Volume Rendering Applications," Computer Graphics Proceedings, Annual Conference Series, 1998, pp. 169-177.

Yamakita, M. et al., "Tele Virtual Reality of Dynamic Mechanical Model," Proceedings of the 1992 IEEE/RSJ International Conference on Intelligent Robots and Systems, Jul. 7-10, 1992, pp. 1103-1110.

Aiger et al., "Real-Time Ultrasound Imaging Simulation," 1998, 24 pages.

Cotin et al. "Real-Time Elastic Deformations of Soft Tissues for Surgery Simulation", IEEE Transactions of Visualization and Computer Graphics, vol. 5, No. 1, Jan.-Mar. 1999, pp. 62-73.

Ehricke, Hans-Heino, "SONOSim3D: A Multimedia System for Sonography Simulation and Education with an Extensible Case Database", European Journal of Ultrasound 7, 1998, pp. 225-230.

International Preliminary Report on Patentability, International Application No. PCT/US2005/031391, dated Apr. 3, 2007.

Japanese Patent Office, Notice for Reasons of Rejection, Application No. 2007-533500, dated May 11, 2010.

Maul et al. "Ultrasound Simulators: Experience with the SonoTrainer and Comparative Review of Other Training Systems", Ultrasound Obstet Gynecol, Aug. 4, 2004, pp. 581-585.

Office Action by UK Intellectual Property Office, Application No. GB0706763, dated Jul. 1, 2010.

Written Opinion of the International Searching Authority, Application No. PCT/US2005/031391, dated Mar. 1, 2006.

United States Patent and Trademark Office, Office Action, U.S. Appl. No. 10/950,766 mailed Dec. 28, 2007.

United States Patent and Trademark Office, Office Action, U.S. Appl. No. 10/950,766 mailed Jun. 28, 2007.

United States Patent and Trademark Office, Office Action, U.S. Appl. No. 10/950,766 mailed Aug. 11, 2008,.

United States Patent and Trademark Office, Office Action, U.S. Appl. No. 10/950,766 mailed Feb. 2, 2009.

United States Patent and Trademark Office, Office Action, U.S. Appl. No. 10/950,766 mailed Jul. 13, 2009.

FIG. 11

DETERMINING LOCATION AND ORIENTATION OF AN OBJECT POSITIONED ON A SURFACE

BACKGROUND

Laparoscopy is a surgical procedure that involves the introduction of surgical instruments through small incisions in the outer layers of skin of a patient. Normally in a laparoscopic procedure, incisions are made to allow the introduction of two or more instruments. The advantage of laparoscopy over "open" surgical procedures is that smaller incisions are made, which enables the patient to recover more quickly than when a larger incision is required. Also, due to the reduced exposure of internal organs to airborne germs during a laparoscopic procedure, the odds of developing an internal infection is reduced.

Normally in laparoscopic procedures, trocars are first positioned through the skin to provide a channel through which other instruments can be inserted. For example, a laparoscopic video camera can be inserted through the trocars to view the patient's internal organs. Other instruments can be inserted as well to perform cutting, removing, stitching, and other surgical actions.

In order to practice the skills necessary to perform laparoscopic procedures or other types of surgical procedures, surgeons in training can sometimes use virtual reality systems, which have been developed in recent years to allow a trainee to practice on virtual patients in a virtual realm. With regard to virtual reality laparoscopic simulators, manipulation of physical handles of laparoscopic tools controls the virtual laparoscopic tools in the virtual realm. By manipulating the tools, the trainee can virtually insert instruments into the abdomen of a virtual patient and perform surgical procedures on the virtual patient.

The location of the physical handles of laparoscopic simulators is usually fixed. Also, the entry location through which the virtual instruments are introduced into the abdomen of the virtual patient is fixed. However, recent developments have been made in the field of laparoscopic simulators to free up each individual laparoscopic instrument. For instance, rather than placing the virtual instruments in a fixed position, manufacturers have created individual modules for each laparoscopic tool to allow placement of each module in any reasonable location.

This development allows a trainee to place tools in positions that may be more ergonomic or comfortable to the trainee. One of the shortcomings of these systems, however, is that the conventional laparoscopic simulators are not designed to correlate the location information of these modules in the physical realm with the location of the virtual instruments in the virtual realm. Therefore, virtual images of a number of laparoscopic tools may not match with the actual physical location of the modules in the real world, which can lead to confusion on the part of the trainee. Also, the trainee may experience an awkward situation where the physically manipulated tools interact with their physical environment in a way that is different from the tool interaction in the virtual realm. Thus, it may be evident that further developments can be made in the current state of the art to address these and other inadequacies of the conventional systems and methods.

SUMMARY

The present disclosure describes systems, methods, and related logic for determining the location and orientation of an object that is placed on a surface. In one particular embodiment, a system comprises an optical device that is physically supported by an object at a fixed position with respect to a reference point of the object. The system also comprises a surface upon which the object can be placed. Applied to the surface is a reference pattern having an array of markings that are visible to the optical device. The array of markings includes encoded location information and orientation information. The system further comprises a processing device that is in communication with the optical device. The processing device is configured to calculate the location and orientation of the reference point of the object with respect to the surface.

Other features, advantages, and implementations of the present disclosure, not expressly disclosed herein, will be apparent to one of ordinary skill in the art upon examination of the following detailed description and accompanying drawings. It is intended that such implied implementations of the present disclosure be included herein.

BRIEF DESCRIPTION OF THE DRAWINGS

The components in the following figures are not necessarily drawn to scale. Instead, emphasis is placed upon clearly illustrating the general principles of the present disclosure. Reference characters designating corresponding components are repeated as necessary throughout the figures for the sake of consistency and clarity.

DETAILED DESCRIPTION

The present disclosure describes systems and methods for determining the location and orientation of an object placed on a surface. Of the various applications for such systems, one application in particular relates to determining the location and orientation of a module used in surgical simulators. In recent developments regarding laparoscopic simulators, for instance, individual modules have been created to allow a trainee to place the modules in any location with respect to a simulated patient. However, the conventional simulators do not correlate the location and orientation of the modules in the physical realm with the location of the virtual instruments in the virtual realm. There is therefore a discontinuity between the freely placed modules and the effect that the location and orientation of the modules can have on a virtual laparoscopic procedure. Because of this discontinuity, the virtual reality display might provide feedback to the trainee that does not correspond accurately with movements in the modules and can therefore be awkward to the trainee.

In order to overcome the deficiencies in the conventional simulators, the present disclosure describes systems and methods for determining the location and orientation of a module or other object when it is placed on a surface. In the laparoscopic simulator environment, for example, the location and orientation of the freely placed modules can be determined. By knowing the location and orientation information of one or more modules, the virtual reality system can provide a more realistic interface. The visual feedback provided to the trainee of the virtual laparoscopic procedure is more accurate and better correlates the physical manipulation with the virtual world.

The manner in which location and orientation information is determined includes the use of an optical device. The optical device may be an image capture device, such as a camera, or may be a scanner, such as a mechanically driven barcode reader, or may be another suitable detection device. The optical device is affixed to an object, such as the moveable module of a laparoscopic simulator. The optical device is directed downward toward the surface on which the module is placed. Again referring to the laparoscopic simulator implementation, the surface may be a representation of the abdomen of the patient. Other parts of the patient's body not including the abdomen can be represented, for example, by a mannequin or other similar model or form.

This particular surface on which the module is place is specifically designed to include an array of patterns or markings that include coded information regarding coordinates of the surface, which thereby correlate to particular parts of the simulated patient's abdomen. The trainee can place each of these modules on the surface in a desired location. Particularly, the location might be chosen by the trainee, for example, such that a reference point of the laparoscopic simulator, such as the physical portion of the simulator that is representatively inserted into the simulated body, is positioned where the entry point allows access to certain organs. The choice of location may depend, for example, on the organs that should be accessed based on the particular surgical procedure being practiced.

When the module is placed in the desired position, the trainee can prompt the system to determine the location and orientation. In response to the prompt, the optical device optically senses a view of the surface or captures an visual image of a portion of the surface, which includes the coded coordinate information applied thereon. A processing device decodes the information from the image to determine the location and orientation of the captured image with respect to the surface. Based on any predefined offset between the location of the captured image and the location of a reference point with respect to the module, i.e. the insertion location of the surgical instrument, the reference point of the module with respect to the surface can then be calculated.

Since the surface associated with the surgical simulation embodiments correlates with the location of the body of the virtual patient, the virtual reality system can provide an accurate simulation of the internal organs encountered depending on the particular placement of the module. In this sense, a trainee can indirectly learn the importance of laparoscopic instrument placement, e.g. trocar placement, by positioning the modules of the laparoscopic simulator in various locations. In reality, placement of trocars can have a large impact on the success of the procedure. Also, proper placement can affect the surgeon's ease of tool manipulation, where, on the other hand, an awkwardly placed instrument might be difficult to maneuver. Depending on the type of surgical procedure being performed, a trainee can learn that trocars should be inserted in certain positions with respect to the surface of the body in order to access specific organs. Therefore, success and ease of tool manipulation in the virtual surgical procedure can be based on this initial laparoscopic instrument placement.

Although many examples described in the present disclosure relate to virtual laparoscopic simulators and other surgical simulators, it should be understood that the scope of the present disclosure is intended to encompass other applications where the position of an object's placement on a surface is to be determined. Other advantages will become apparent to one of ordinary skill in the art from an understanding of the present disclosure.

Figure 1A:
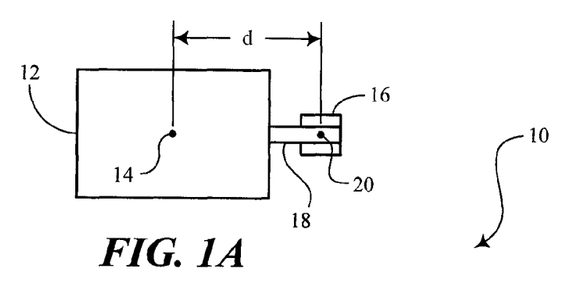
FIGS. 1A, 1B, and 1C illustrate top, front, and side views of a system for determining the location and orientation of an object according to one embodiment.
Figure 1B:
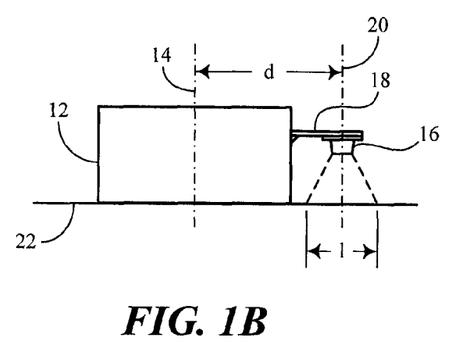
Figure 1C:
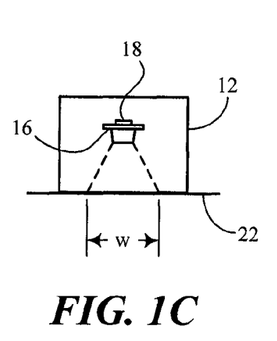

FIGS. 1A through 1C show top, front, and side views, respectively, of an embodiment of a system 10 for determining position information, e.g., location and angular orientation, of an object placed on a surface. In this embodiment, system 10 includes an object 12 having a reference point 14. Connected to object 12 is an optical device 16 supported by a support structure 18 that fixes optical device 16 to object 12. In alternative embodiments, optical device 16 includes a scanner, such as a mini flat bed scanner or mechanically driven barcode reader, which can be placed on the bottom of object 12. A reference point 20 is associated with optical device 16 and may correspond to the center of view of optical device 16. Object 12 can be positioned in any location and oriented at any rotational angle with respect to a surface 22, as long as there is sufficient space for the object 12 in the particular location and orientation.

Reference point 14 with respect to object 12 is used as a reference for determining the location of the object 12. It should be understood that reference point 14 can be located at the center of mass of object 12 or at any other point associated with object 12. In some embodiments, reference point 14 may be located at a point in space outside the boundary of object 12. If surface 22 is flat, for example, reference point 14 may be considered to be a reference axis, as shown, which runs perpendicular to surface 22. Likewise, reference point 20 of optical device 16 can be located at any point with respect to optical device 16 or with respect to the viewing orientation of optical device 16. Reference point 20 in some embodiments can be considered to be a reference axis, such as a reference axis perpendicular to a flat surface.

Although not shown specifically in FIG. 1, surface 22 includes an array of patterns or markings thereon that provide visual information pertaining to location. Details of embodiments of arrays of markings are described below with respect to FIGS. 3-6. When optical device 16 optically senses features of surface 22 or captures an image of the markings on surface 22, the sensed or captured image can be analyzed to determine the location and orientation of reference point 20 with respect to surface 22. Knowing the offset distance d between reference point 14 of object 12 and reference point 20 of optical device 16, the location and orientation of object 12 can be calculated from the location and orientation information determined with respect to optical device 16.

Object 12 represents any sufficiently portable unit or module that can be placed on surface 22. Depending on the size and shape of object 12 and the dimensions of surface 22, any suitable number of similar objects 12 can be placed on surface 22. With similar image sensing capabilities, the location and orientation of each of the other objects with respect to surface 22 can be determined as well.

During assembly of object 12 or during connection of optical device 16 to object 12, many factors may affect the viewable frame size of optical device 16 with respect to actual dimensions on surface 22. For example, frame size can be affected by the height that optical device 16 is positioned above surface 22. Also, the viewing angle of optical device 16 can affect the frame size. The ratio of the size of the viewable frame of optical device 16 to the size of the patterns on surface 22 can be established during assembly. One design consideration regarding a proper ratio may depend on the distance between corresponding parts of adjacent markings. If the distance between corresponding parts is about one inch, the frame size should be set to be able to view at least one whole marking, which, in this case, has a size of about 1.4 inches by 1.4 inches. With respect to embodiments in which optical device 16 is a scanner located on the bottom of object 12, the scanner includes a scanning area approximately equal to the size of the scanner itself.

Regarding particular embodiments in which the geometric dimensions of the patterns are used to determine coordinate information, as described in more detail below, the ratio can be used to calculate the actual dimensions of these patterns. In some embodiments, optical device 16 can be calibrated if necessary to adjust the size of the image frame with respect to actual surface 22 dimensions. In addition, system 10 may also include means for recalibrating optical device 16 in the field when needed. Furthermore, when the distance between optical device 16 and surface 22 is set, a focal length, depending on the type of optical device 16 being used, can also be established.

Another consideration in the construction of system 10 is the resolution of optical device 16. Depending on the resolution of the patterns or markings on surface 22, optical device 16 should have sufficient resolution to detect the patterns or marking to such an accuracy to be able to distinguish between two different patterns or markings. In some embodiments, optical device 16 may have a resolution of about 500 pixels by 500 pixels. Also, optical device 16 may be positioned on object 12 about one inch above surface 22 such that the frame size would be about one square inch. In this example, assuming that the frame size is one inch by one inch and the resolution is 500 by 500, optical device 16 may be able to detect differences in patterns or markings of about 0.002 inches.

Figure 1D:
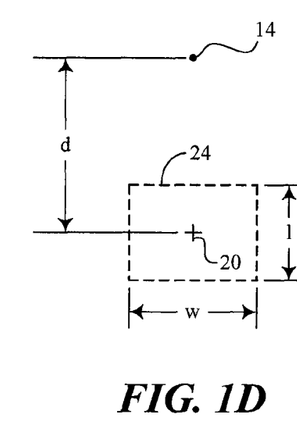
FIG. 1D is a diagram illustrating a frame view of the optical device shown in FIGS. 1A-1C according to one embodiment.

FIG. 1D shows an example of a frame 24 of an image viewed by optical device 16. Also shown in FIG. 1D is reference point 20 of optical device 16, which in this example is aligned with cross-hairs at the center of frame 24. Frame 24 in this example has a width of "w" and a length of "1". Also, the distance d is shown from reference point 20 to reference point 14.

Figure 2:
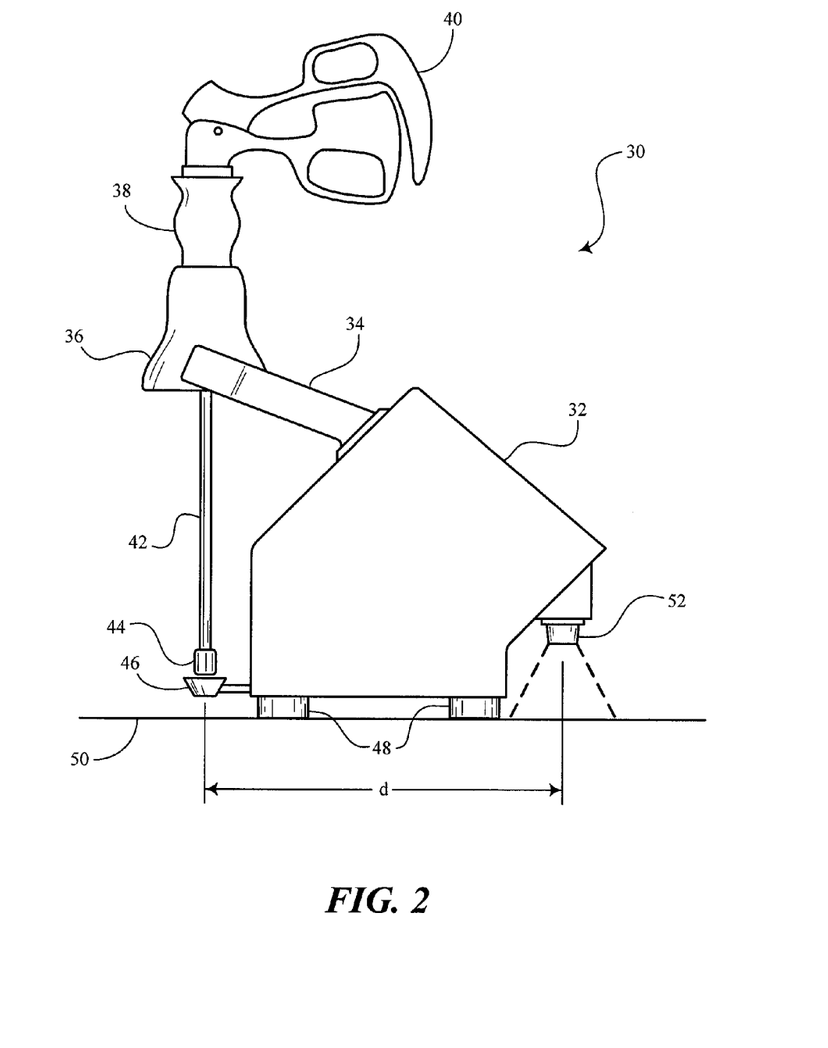
FIG. 2 is a diagram of a laparoscopic simulator module according to one embodiment.

FIG. 2 shows an embodiment of a laparoscopic simulation module 30. In this implementation, laparoscopic simulation module 30 includes a base 32, arm 34, and sleeve 36. Manipulated components of laparoscopic simulation module 30 include a neck 38, which is connected to handle 40 and shaft 42. Handle 40 can be designed to have the same look and feel as the handle of actual trocars or other laparoscopic instruments. In a rest position, neck 38 is placed in sleeve 36 and tip 44 of shaft 42 is placed in pocket 46. The location of shaft 42 in the rest position may be used to represent an entry point, or virtual incision location, where the respective laparoscopic instrument is inserted through the skin of the virtual patient.

When the user pulls handle 40 in an upward direction, neck 38 is removed from sleeve 36 and tip 44 is removed from pocket 46 to allow shaft 42 to move through sleeve 36 in an upward or downward direction. Handle 40 may also be tilted backward or forward by rotating sleeve 36 with respect to arm 34, which can pivot up or down. In addition, arm 34 is configured to pivot from side to side in response to movement of shaft 42.

Laparoscopic simulation module 30, as shown in FIG. 2, further includes feet 48 on the underside of base 32. In some embodiments, feet 48 may include suitable mechanisms for temporarily attaching laparoscopic simulation module 30 to surface 50 for stability. In alternative embodiments, attaching mechanisms can be fixed to base 32 for holding laparoscopic simulation module 30 in place with respect to surface 50. Therefore, when the user manipulates handle 40, base 32 remains stationary. When base 32 is firmly held in a fixed position on surface 50, the position and orientation of laparoscopic simulation module 30 can be determined according to the teaching herein.

Laparoscopic simulation module 30 also includes an image capture device 52 or other suitable type of optical device for sensing visible or invisible markings of surface 50. In some embodiments, image capture device 52 includes a scanner, which can be located on the bottom of base 32. Image capture device 52 is oriented in a downward-viewing direction in order to view a portion of the top of surface 50. A reference position with respect to image capture device 52 may include the center of the viewable frame of image capture device 52 or a reference axis of image capture device 52 when oriented to view surface 50 in a perpendicular direction.

An offset distance "d" from this reference position to the rest position of shaft 42 is predetermined during assembly of laparoscopic simulation module 30. As shown in this embodiment, image capture device 52 is positioned on the opposite side of base 32 from shaft 42, but in other embodiments image capture device 52 may be positioned closer to the location of shaft 42. By reducing the offset distance d between reference points, fewer markings would be needed on surface 50 since the markings can be viewed near the reference point of shaft 42 to be positioned over the same possible area on surface 50. As mentioned earlier, the initial location of shaft 42 in the rest position in pocket 46 can be used as the reference point where a trainee virtually inserts the laparoscopic instrument, e.g., trocar, into the abdomen of the virtual patient. In this regard, the body of the virtual patient is represented by surface 50. By associating physical features of the virtual patient either applied on surface 50 or represented in other suitable ways, the trainee can determine a desired location where the virtual tool is to enter the abdomen.

Image capture device 52 is configured to capture an image of surface 50 after laparoscopic simulation module 30 has been positioned by trainee and temporarily locked in place. Surface 50 includes patterns or markings that are described in more detail with respect to FIGS. 3-7. A portion of surface 50, including at least one marking, is viewed with the image frame of image capture device 52. When position of laparoscopic simulation module 30 is securely positioned, image capture device 52 records a sensed image of surface 50. From this image, the location and orientation of image capture device 52 with respect to surface 50 can be determined. Then, based on knowledge of the offset distance d, the location and orientation of the reference point, e.g., shaft 42, of laparoscopic simulation module 30 with respect to surface 50 can also be determined. Since the surface 50 corresponds to locations of the abdomen of the virtual patient, the position of the reference point of laparoscopic simulation module 30 with respect to the virtual patient can be determined. Furthermore, movements of handle 40 by a trainee are sensed and used to move virtual laparoscopic instruments in the virtual realm with respect to the determined initial entry point through the skin of the virtual patient.

Image capture device 52 may comprise any suitable image sensing devices and associated circuitry, such as, for example, an OEM camera. The viewing angle of image capture device 52 may be any suitable angle to be able to visually capture an area large enough on surface 50 to observe at least one whole marking. For instance, the viewing angle may be fairly wide, such as about 45°. The resolution of image capture device 52 may have any suitable acuity for detecting the particular characteristics of the markings on surface 50. For instance, the resolution may be about 500 by 500 pixels. Assuming that the height of image capture device 52 above surface 50 is about one inch and the viewing angle is such that the frame size is about one inch by one inch, then a resolution of 500 by 500 would allow image capture device 52, when focused properly, to theoretically observe particular differences in the markings of 1"/500, or 0.002 inches. To allow for various errors, however, the markings might be created with distinguishable characteristics of at least about 0.02 inches.

FIGS. 3-6 are diagrams illustrating embodiments of arrays of patterns or markings that can be applied to a surface, particularly a surface on which an object is to be placed. An optical or visual sensing mechanism, such as an image capture device, for example, can be used to view visible or invisible markings on a portion of the surface. Enough of the surface is viewed to detect at least one marking in order to be able to determine where the object is located with respect to the surface. From this, the rotational orientation of the object can be determined as well. The various arrays of markings of FIGS. 3-6 can be used, for example, in conjunction with system 10 of FIGS. 1A-1C, laparoscopic simulation module 30 of FIG. 2, or other systems where an object supports an optical device or image capture device that views a coordinate-encoded surface on which the object is supported.

The markings can be applied to the surface using any suitable application technique. A few non-limiting examples of application techniques include printing the markings directly on the surface, adhering a diagram of the markings to the surface, etching the marking on the surface, or other suitable techniques. The x- and y-axes shown in FIGS. 3-6 are illustrated merely for the purpose of pointing out how the markings are encoded to represent a coordinate system of the surface. Thus, the application of the x- and y-axes on the surface may be omitted.

Each marking in an array includes a feature that is common to all of the other markings of the array. In this way, the common feature can be used as a reference point from which useful information can be extracted. The distance between corresponding portions of the common features of adjacent marking is predetermined based on the frame size of the optical device. This distance, or pitch, may be about 0.7 inches, for example, which would allow a frame size of the captured image to be about one inch by one inch in order that at least one full marking can be viewed.

The coordinate systems shown in FIGS. 3-6 are not necessarily drawn to scale. Although the drawings may show the markings having a pitch of about one inch, the pitch may instead be any other suitable spacing. Also, FIGS. 3-6 merely illustrate a portion of the array, i.e., about a 3×5 pattern. However, it should be understood that the array can be any suitable size. In laparoscopic examples, for instance, if a table or surface is used for representing the abdomen of a regular sized human patient, the surface might be about 18"×18". The surface representing a small child might be about 12"×12", and for a large adult, the surface might be about 24"×24". If there is one marking every 0.7", for example, and assuming that the surface is 18"×18", then the array may include about 25×25, or 625, markings.

The coordinate system established by the array of markings relates to particular features on the surface. In the virtual surgical simulator embodiments, the surface can represent a patient. In other embodiments, the coordinates of the surface may correspond to other features.

In the array, each marking is different from the others in order to include coded information particularly pertaining to that marking. In FIGS. 3-6, the differences between adjacent markings may be slightly exaggerated as shown in order to illustrate the encoding scheme of the particular array of markings. Each marking includes coded information that indicates the coordinate points of that marking with respect to the surface. A processor associated with an object that is to be placed on the surface is configured to decode the markings to determine the coordinate information. Depending on the type of array being used and the particular encoding scheme, the processor is programmed to understand and decode the encoding scheme. The encoding information can be related primarily to the coordinate information of each marking. Rotational orientation information can be extracted from the viewed image of the surface by processing functions, such as rotating the image until it aligns with an expected angle.

Figure 3:
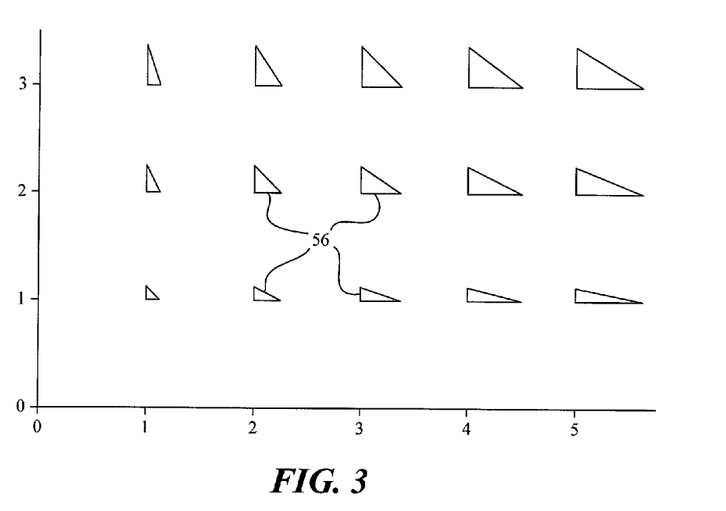
FIG. 3 is a diagram illustrating an example of an array of markings applied to a surface according to a first embodiment.

FIG. 3 illustrates a first embodiment of an array of markings 56 that are applied to a surface. Markings 56 in this embodiment are shown as triangles, each having a different size. The triangles include a right angle at the lower left corner when viewed in the manner as illustrated. Any portion of triangle, e.g., the corner of the triangle at the right angle, may be used to represent a reference point for the respective marking. For example, the marking at coordinate position (1, 2) is shown such that the corner is positioned at the (1, 2) point with respect to the surface. The right angle of the respective triangle may also be used to determine rotational orientation. For example, if an image of a marking is rotated by a certain angle, the processor can perform a rotation function to determine the relative orientation of the image and then ultimately the object.

The triangles are encoded in a matter such that the length of one side of the triangle relates to a first coordinate within the array and another side of the triangle relates to a second coordinate within the array. Particularly, the length of the side along the x-axis of each triangle may be equal to a multiple of a unit length. For example, assuming that a unit length is predefined as 0.04 inches, the length of sides of triangles parallel to the x-axis and located at a third position ("3") along the x-axis will be 0.04 multiplied by 3, which is equal to 0.12 inches. Thus, the triangle's side parallel to the x-axis would be 0.12 inches. At a first position along the x-axis, the length will be one unit; at the second position, the length will be two units; and so on.

Likewise in the y-direction, the length of the side along the y-axis of each triangle may be equal to a multiple of a unit length, which may be the same as the unit length in the x direction, but, in other embodiments, may be different. As an example, at a (x, y) position of (4, 3), the length of side parallel to the x-axis would be four units and the length of side parallel to the y-axis would be three units. The hypotenuse of the triangles is not used in the calculation of coordinates in the embodiment, but may be used as a check if necessary. Otherwise, the hypotenuse may be omitted, such that each marking includes only two perpendicular lines rather than a triangle.

In FIG. 3, the differences in lengths between adjacent triangles are exaggerated for illustration purposes only. In many implementations, however, the differences in lengths may be much shorter. It should be noted that the type of print, or other application technique, used to create the markings on the surface should have sufficient resolution to allow the proper decoding between these different lengths to thereby allow the processor to distinguish between them.

To account for some extreme cases, such as extremely oblong triangles, the triangles in some implementation can include a minimum length "m" and each triangle along an axis can be incremented by a unit length "a". In this case, the first triangle along the axis will have a length of m, and subsequently the lengths would be m+a, m+2a, m+3a, m+4a, etc. In other embodiments, a special mark may be used to indicate which angle is the right angle. In these examples, the processor can decode the triangle lengths without confusing the hypotenuse with another side of the triangle.

Figure 4:
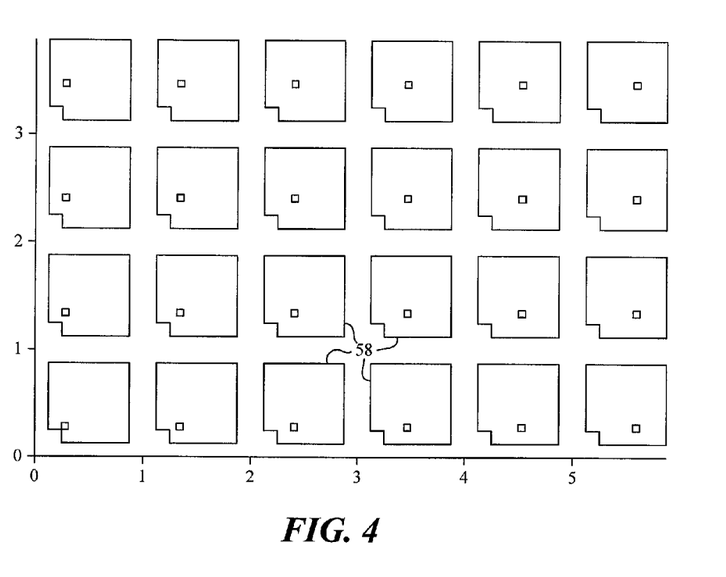
FIG. 4 is a diagram illustrating an example of an array of markings applied to a surface according to a second embodiment.

FIG. 4 illustrates a second embodiment of an array of markings 58 that are applied to a surface. Markings 58 in this embodiment include boxes having a notch in the lower left corner of the boxes. Markings 58 further include small squares, or other geometric shape, positioned within the boxes in a location corresponding to the respective coordinate location of a particular marking 58 with respect to the entire array. For example, the small squares within the boxes having a higher x coordinate will be positioned farther to the right in the boxes. The notch of the box can be used as a common feature of the array to reference a particular location in the coordinate system and to be used for determining rotation orientation information of a captured frame view. It should be noted that this embodiment does not include a point on the respective marking that is located at the coordinate point location. A distance from a common feature on a marking to the coordinate point may be established in this case to account for the positioning of the markings.

Figure 5:
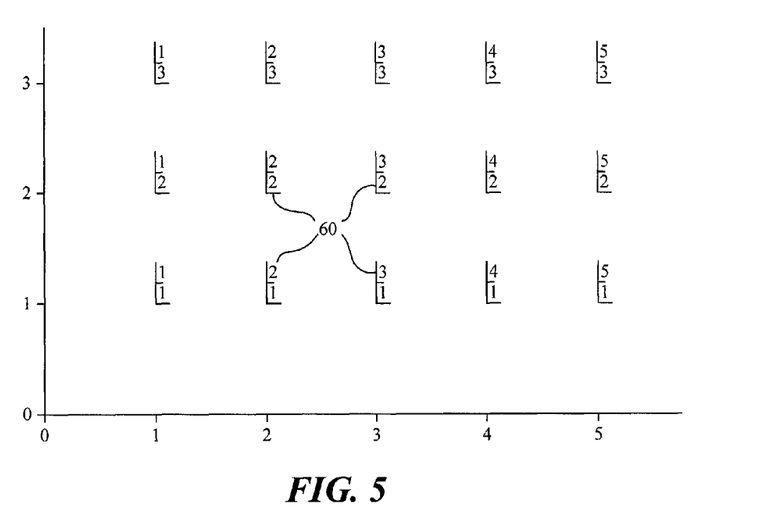
FIG. 5 is a diagram illustrating an example of an array of markings applied to a surface according to a third embodiment.

FIG. 5 illustrates a third embodiment of an array of markings 60 that are applied to a surface. Markings 60 in this embodiment include lines forming a right angle for defining a common feature of each marking 60 and for providing a reference angle for determining angular orientation. Also, each marking 60 include numerical information that corresponds to the coordinate system of the array. In this example, the x value is placed in a top position of marking 60 and the y value is placed in a bottom position of marking 60. In other embodiments, these coordinates can be switched if desired. In the implementation of FIG. 5, a processor configured to decode the coordinate information may include character recognition capabilities. In this respect, the characters representing the coordinates in this embodiment can be numerals and/or alphabetic letters. From the recognized characters, the coordinate point of the respective marking can be determined.

Figure 6:
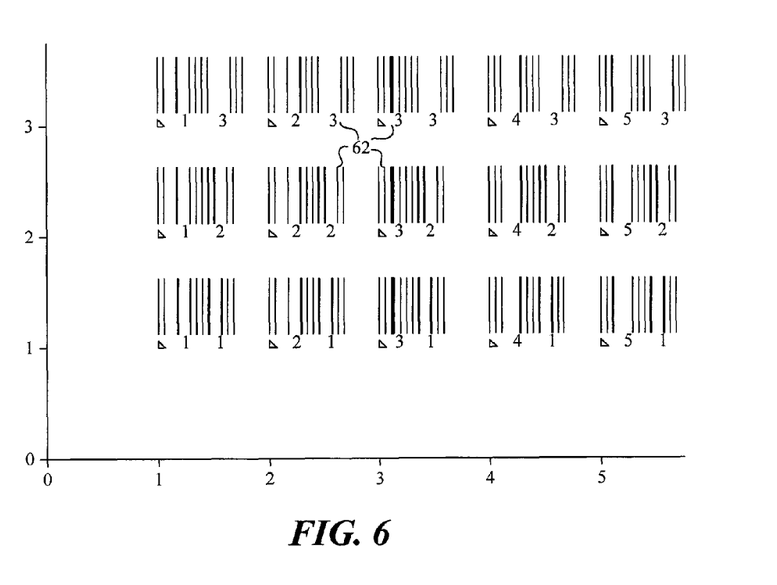
FIG. 6 is a diagram illustrating an example of an array of markings applied to a surface according to a fourth embodiment.

FIG. 6 illustrates a fourth embodiment of an array of markings 62 that are applied to a surface. Markings 62 in this embodiment are shown as bar codes. In addition to the bar codes, markings 62 may also include the numerical characters represented by the bar codes. Also shown in this embodiment associated with each marking 62 is a small right triangle at the bottom left corner intended to provide a reference point. Bar codes are typically encrypted in such a way that the code can only be read in one orientation, i.e., right side up, the small right triangles may be omitted. When present, however, the small right triangle can be used for decoding the angular orientation of a viewed image frame. Otherwise, features of the bar code itself can be used to provide sufficient orientation information for determining rotational angle. In other embodiments, the small right triangle can be replaced with other kinds of encoding patterns for designating a reference point and/or reference angle.

Bar codes of markings 62 define the respective coordinate points for the particular marking 62. Bar codes can include line width and space width information as is used in a typical bar code system, or the bar codes herein can use other suitable encoding schemes understandable to a corresponding processor configured to decode the bar codes.

These and other embodiments for encoding coordinate information on a surface can be used in systems for determining the location and orientation of an object placed on the surface. For example, other embodiments may include color encoding schemes, texture encoding schemes, holographic encoding schemes, grayscale encoding schemes, non-visible light encoding schemes, or other suitable encoding schemes to create an array of markings that can communicate location and orientation information of the marking with respect to a coordinate system of a surface.

Figure 7:
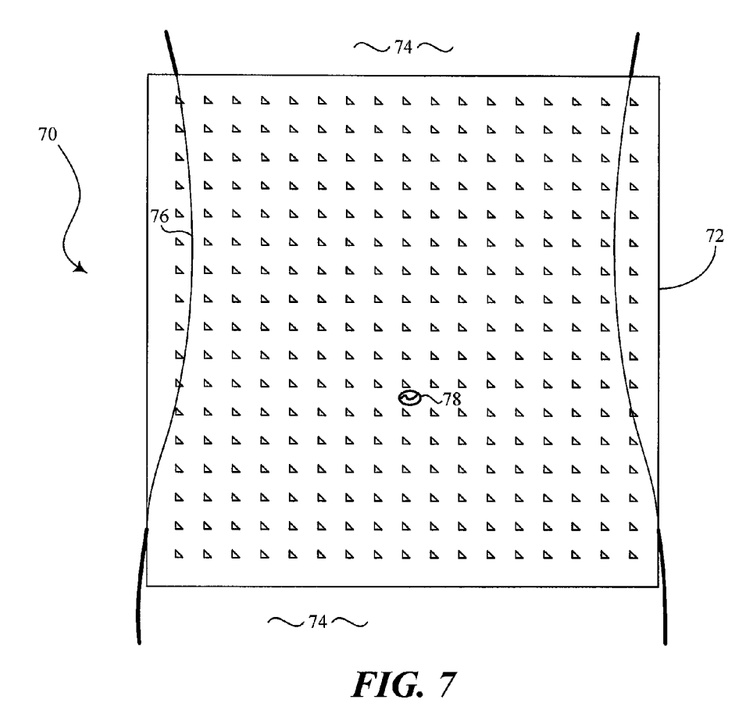
FIG. 7 is a diagram illustrating a surface having an array of markings for use in laparoscopic simulation according to one embodiment.

FIG. 7 illustrates an embodiment of a dummy patient 70 that can be used in a surgical simulation system. For example, dummy patient 70 may be used in conjunction with laparoscopic simulation module 30 of FIG. 2. Dummy patient 70 in this implementation includes a surface 72 having an array of markings applied thereon. Surface 72 may represent a portion of the body of dummy patient 70 that corresponds, for example, with the lower thorax and/or abdomen. This area of the body is an area that might be used in a number of laparoscopic simulation procedures. In addition to surface 72, dummy patient 70 may optionally include a mannequin 74 or other form or model representing features of a patient. In FIG. 7, only a small portion of mannequin 74 is shown, but in some embodiments, mannequin 74 may include a life size replica of a human body. Generally, mannequin 74 is used as a reference for showing the outline of the dummy patient 70 and may additionally include locations where laparoscopic instruments are inserted.

In some embodiments, surface 72 includes an outline 76 of the patient and an image of a belly button 78. Outline 76 and belly button 78 are used to aid the trainee in the placement of a module with respect to certain physical features of the patient's body. Also applied to surface 72 are markings, which may include the arrays mentioned with respect to FIGS. 3-6 or other suitable arrays. In some embodiments, outline 76 and belly button 78 can be applied to surface 72 in a different print, color, line thickness, etc. from the markings to allow a processor to easily distinguish representative body parts from the markings used to determine location. Alternatively, these lines can be created such that they discontinue near potential intersections with the markings. Outline 76 and belly button 78 may be printed using an ink that is visible to the trainee but invisible to the optical device that views the markings on surface 72. Outline 76 and belly button 78 are created so that they do not interfere with or invalidate the markings.

Outline 76 and belly button 78 can be optional in this embodiment, but are helpful to show the location of certain features of the body when the trainee attempts to position the surgical module, e.g., laparoscopic simulation module 30, in an ideal position with respect to the patient. Depending on size of the surgical modules and surface 72 on which the modules are placed, it may be possible for the trainee to arrange up to about 5 or 6 modules on surface 72.

In many embodiments, surface 72 of dummy patient 70 is flat in order to simplify the calculations with respect to the orientation of the modules. However, in other embodiments, surface 72 can be contoured to better resemble the human body, which in this case increases the complexity of calculations with respect to rotational angles. A contoured surface can be mapped, for example, to correlate particular locations on the surface with a predetermined z-axis dimension with respect to a reference xy plane and with predetermined pitch and roll angular rotations. Dummy patient 70 can be constructed to have any size, gender, age, etc. as desired. Multiple dummy patients can be created to allow the trainee to practice surgical procedures on different types of body shapes and sizes.

The markings of surface 72 shown in FIG. 7 are not shown as being distinct from each other as described with respect to FIGS. 3-6. However, in practice, the markings will have any suitable distinction to provide proper location information as described above. Particularly, every marking will be different from the others to encode specific coordinate information of the respective marking.

Figure 8:
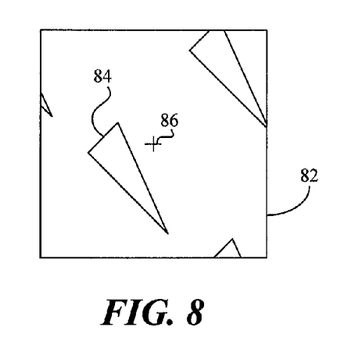
FIG. 8 is a diagram illustrating an example of an image of a surface having an array of marking captured by an optical device according to one embodiment.

FIG. 8 illustrates a frame view 82 captured by an optical device of a portion of a surface having markings 56 as shown in FIG. 3. Frame view 82 includes at least one whole marking 84 and portions of other markings. From marking 84, the location of a reference point, such as cross-hairs 86, of frame view 82 can be determined with respect to the surface. The specific calculations used to determine location and orientation information from image view 82 are described in more detail below with respect to FIGS. 9 and 10.

Figure 9:
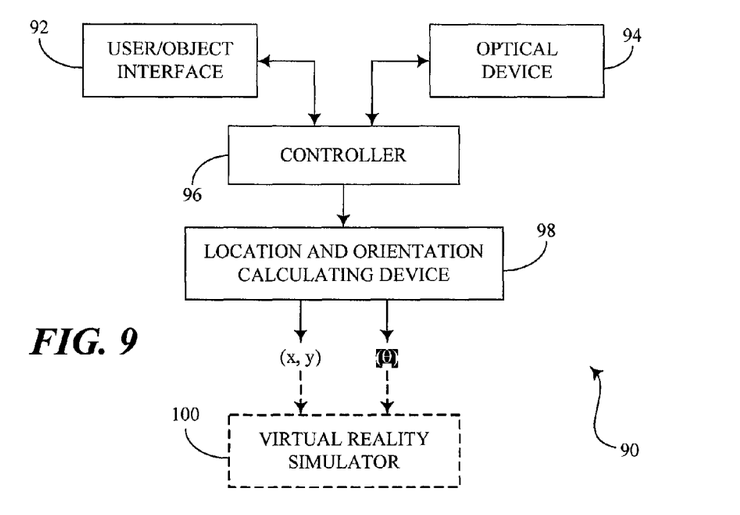
FIG. 9 is a block diagram of an object placement analyzing system according to one embodiment.

FIG. 9 is a block diagram showing an embodiment of an object placement analyzing system 90. In this embodiment, object placement analyzing system 90 includes a user/object interface 92, optical device 94, controller 96, and location and orientation calculating device 98. A first output of location and orientation calculating device 98 provides location information with respect to a planar surface, represented here using coordinates (x, y) in the xy plane. A second output provides information related to an angular yaw orientation θ rotated about a z-axis perpendicular to the xy plane.

When object placement analyzing system 90 is used to determine the location and orientation of a simulation module on a surface, the outputs from location and orientation calculating device 98, i.e., (x, y) and θ, are used in virtual reality simulator 100. For surgical simulators, such as laparoscopic simulators, the location and orientation information can be used as initial insertion or incision points relative to the anatomy of the virtual patient. As mentioned above, these initial points can affect what organs can be easily accessed or reached and may affect the success of particular surgical procedures.

User/object interface 92 includes input and output devices allowing communication between the user and the object to be positioned on the surface. Object placement analyzing system 90 is supported on or in the object, but in other embodiments may include elements located remote from the object. Input/output devices of user/object interface 92 may include input mechanisms such as buttons, switches, keyboards, keypads, cursor control devices, computer mice, or other data entry devices. Output devices may include display panels, LEDs, computer monitors, virtual reality display devices, audio output devices, printers, or other suitable peripheral devices.

User/object interface 92, for example, may include a START button or switch allowing the user to start the analysis of the placement of an object. In response to startup, user/object interface 92 may provide an output to the user to instruct the user to position the object of which the position is to be analyzed on a surface having encoded location information. Also, an output may be provided to the user to instruct the user to lock the object in place with respect to the surface, if necessary. Once the user has positioned the object on the surface and locked it in place, the user indicates that he is ready to proceed, such as by pressing a GO or PROCEED button, for example.

Then, with the object in position, controller 96 instructs optical device 94 to optically sense or capture an image of a portion of the surface on which the object is placed. Controller 96 then forwards the image information from optical device 94 to location and orientation calculating device 98. Location and orientation calculating device 98 uses certain processing algorithms to determine the location and orientation of the object. The location information is output from location and orientation calculating device 98 as (x, y) coordinates with respect to the planar surface. Also, angular information is output as θ with respect to an angular rotation about the z axis. With respect to the embodiments in which the surface is not planar, such as a surface contoured as the shape of a human body, additional information may be calculated by location and orientation calculating device 98. Thus, instead of three degrees of freedom, i.e., (x, y) spatial information and θ rotational information, six degrees of freedom may be calculated.

The above examples refer to a "detect once" mode in which the object is placed on the surface and object placement analyzing system 90 detects the position and orientation of the object only once, until prompted to repeat the detection. Furthermore, object placement analyzing system 90 can also be used in an interactive mode in which current position information is fed back to the user continually and in real-time. In this mode, user/object interface 92 may include a display screen showing updated position information of the object with respect to the surface. In the surgical simulator examples, virtual surgical tools can be shown with respect to the virtual patient in the interactive mode. In addition, feedback can be provided to the user indicating the location of a virtual tool versus where the tool should be. Thus, in an interactive manner, the trainee can learn tool placement strategies depending on the selected surgical procedure.

Location and orientation calculating device 98 may further determine when the detected image include invalid information. For example, if the markings are no longer in view or out of focus, then it is likely that the object or module has been picked up off the surface. When the object is returned to the surface, location and orientation calculating device 98 can determine the position information again.

In some implementations, the (x, y) and θ information can be used in a virtual reality simulator 100. With the location and orientation information calculated by location and orientation calculating device 98, virtual reality simulator 100 can determine a reference position in a virtual environment. For instance, the placement information can relate to an initial point where a virtual laparoscopic tool is inserted into the virtual patient. The entry point relative to the anatomy of the virtual patient can affect what organs can be reached and the difficulty in executing the virtual surgical procedures.

Figure 10:
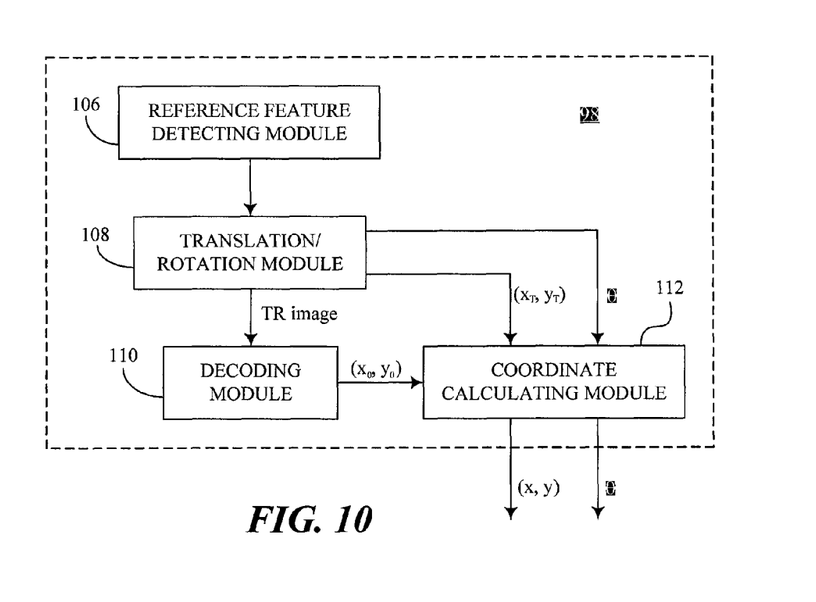
FIG. 10 is a block diagram of the location and orientation calculating device shown in FIG. 9 according to one embodiment.

FIG. 10 is a block diagram of an embodiment of location and orientation calculating device 98 shown in FIG. 9. In this embodiment, location and orientation calculating device 98 includes a reference feature detecting module 106, a translation/rotation module 108, a decoding module 110, and an coordinate calculating module 112.

Reference feature detecting module 106 analyzes the image frame to detect one or more whole markings in the array of markings on the surface. In some embodiments, two or more markings may be used to determine distance if necessary for interpolating position with respect to the markings. In other embodiments, a single marking can be used to gather the necessary information needed to determine location and orientation. When a single marking is used, reference feature detecting module 106 analyzes the marking to find a mark or feature that is common to all markings of the array on the object-supporting surface. For example, the reference feature may be a right angle of a triangle, a characteristic, feature, shape, or other distinctive aspect that is shared by the particular array of markings applied to the surface.

Translation/rotation module 108 performs translation and rotation procedures on the marking, in any particular order. Translation includes graphically moving the points of the marking such that a particular reference point of the marking is aligned with a reference point on the frame view. For example, the marking may include a corner of a right angle or other point associated with other respective features of the marking. Translation in this case may include moving the marking until the particular reference point of the marking is matched up with the reference point of the frame view, which may be represented by the cross-hairs at the center of the frame view. The translation process involves determining a distance that the marking is moved to line up with the reference point of the frame view as well as the displacement in both the x and y directions. Particularly, the distances and displacements are determined relative to dimensions of the surface itself, which may require knowledge of predetermined ratios between surface dimension and frame view dimensions.

Rotation includes rotating the marking about the reference point of the marking until a reference angle of the marking, such as a right angle, matches a reference angle of the frame view, such as the angle of cross-hairs in the frame. This rotation technique determines the rotational angle, or yaw, about the z-axis perpendicular to the xy plane of the surface. These and other techniques for determining translation and rotation may be used as desired. After translating and rotating a marking, translation/rotation module 108 outputs the translated and rotated image ("TR image") to decoding module 110. In addition, translation/rotation module 108 outputs the x and y displacements $(x_T, y_T)$ of the translation from the reference point of the marking to the reference point of the frame view. The $(x_T, y_T)$ information as well as the rotational angle θ is provided to coordinate calculating module 112.

With the translated and rotated marking aligned in a predetermined manner, decoding module 110 is able to extract the portions of the marking from the TR image that include encoded coordinate values of the marking. For example, in the embodiment using triangles, decoding module 110 extracts the length of sides of the triangles to be used to decode the (x, y) coordinates. If the markings include characters, such as numerals for designating coordinates, then decoding module 110 may include character recognition functions to extract these characters. In the bar code embodiment, decoding module 110 decodes the bar code information to determine coordinates. Depending on the particular encoding scheme in use, decoding module 110 extracts and decodes the necessary information as needed. From the encoded information, decoding module 110 is configured to determine coordinates $(x_0, y_0)$ representing the coordinates of the particular marking.

Coordinate calculating module 112 receives coordinates $(x_0, y_0)$ from decoding module 110 and receives translation coordinates $(x_T, y_T)$ and rotational information θ from translation/rotation module 108. Coordinate calculating module 112 sums the coordinates $(x_0, y_0)$ with the coordinates $(x_T, y_T)$ to calculate an exact location of the frame view. The translation coordinates $(x_T, y_T)$ can be considered to be interpolation or extrapolation information between respective markings or from a single marking. By combining these values, coordinate calculating module 112 calculates frame coordinates $(x_f, y_f)$ and the angle θ remains the same. Specifically, $x_f=x_0+x_T$ and $y_f=y_0+y_T$.

In the embodiments in which there is an offset between the reference point of the image frame and the reference point of the object, coordinate calculating module 112 further compensates for this offset. Since the offset from the reference point of the image frame to the reference point of the object can be established during assembly of the object as a vector having an x component and a y component, i.e., $x_d$ and $y_d$, where d is related to the distance d as shown in FIG. 1 or FIG. 2. The reference point of the object (x, y) can then be determined from $(x_f, y_f)$ using the offset vector. Specifically, $x=x_f+x_d$ and $y=y_f+y_d$.

Object placement analyzing system 90 and location and orientation calculating device 98 may include one or more processors, such as a general-purpose or specific-purpose processor or microcontroller. The processors may operate in conjunction with a suitable memory, which may include internally fixed storage and/or removable storage media for storing information, data, and/or instructions. The storage within the memory components may include any combination of volatile memory, such as random access memory (RAM), dynamic RAM (DRAM), etc., and/or non-volatile memory, such as read only memory (ROM), electrically erasable programmable ROM (EEPROM), flash memory, etc. Memory can also store a software program that enables processor to execute the calculations of location and orientation information of an object placed on a surface as described herein.

Various logical instructions or commands of location and orientation calculating device 98 may be included in the software program for calculating location and orientation. Any or all of the components of location and orientation calculating device 98 of the present disclosure can be implemented in hardware, software, firmware, or a combination thereof. When implemented in software or firmware, the software can be stored in memory and executed by a processor. When implemented in hardware, location and orientation calculating device 98 can be implemented, for example, using discrete logic circuitry, an application specific integrated circuit (ASIC), a programmable gate array (PGA), a field programmable gate array (FPGA), etc., or any combination thereof. Any programs or software code related to the disclosed elements described herein may include executable logical instructions that can be embodied in any suitable computer-readable medium for execution by any suitable processing device. The computer-readable medium can include any physical medium that can store the programs or software code for a measurable length of time.

Figure 11:
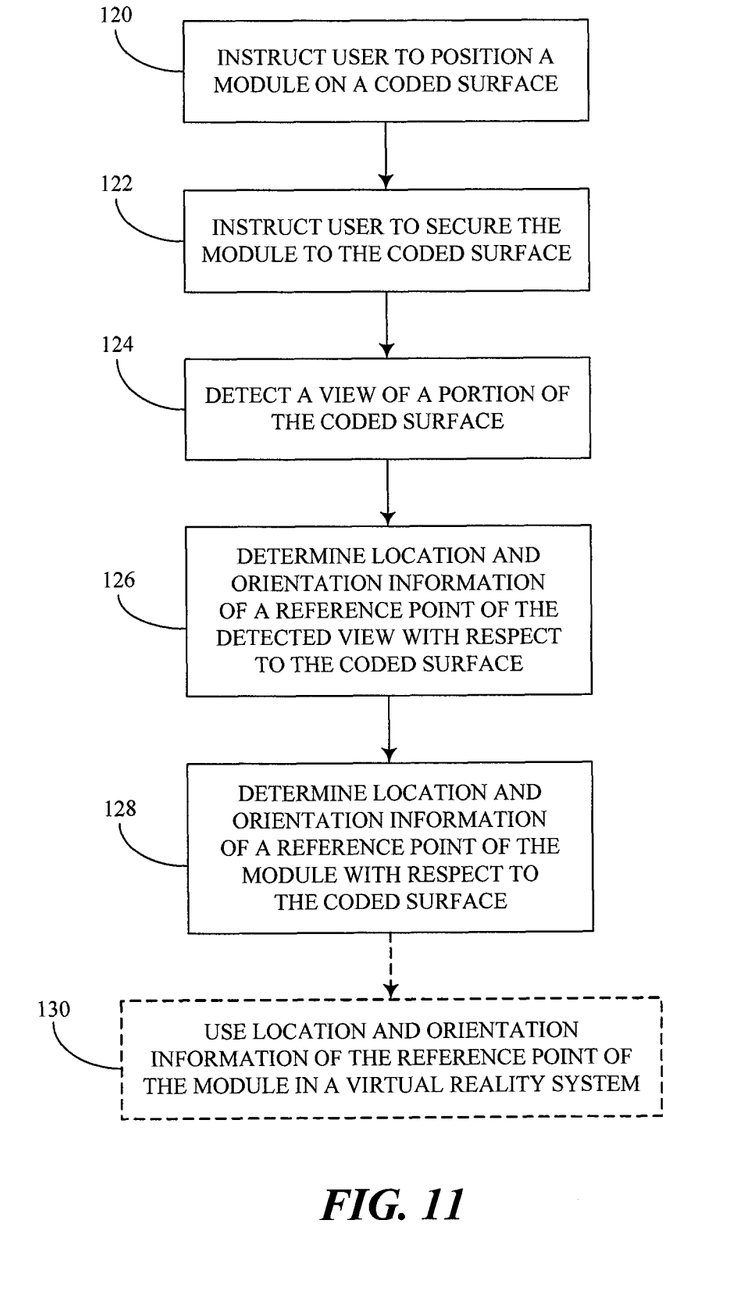
FIG. 11 is flow chart illustrating a method of operating an object placement analyzing device according to one embodiment.

FIG. 11 is a flow chart illustrating an embodiment of a method for determining location and orientation of a module to be positioned on a surface, which may be flat or contoured. The method in this embodiment includes instructing a user to position the module in any desirable location and orientation on a coded surface, as indicated in block 120. In particular, the module in this example may include image capture capabilities. The surface on which the module is placed can be encoded with a specific array of markings having any desirable encoding scheme for indicating coordinate positions with respect to the surface. After the user has placed the module on the surface, the user may provide an indication that the module has been so placed. In block 122, the user is instructed to secure the module to the coded surface. After securing the module, the user may further provide an indication that the module has been secured as instructed.

In block 124, the method includes detecting or sensing a view of a portion of the coded surface, such as by using an optical device or image capture device. This view include a sufficient portion of the surface to allow for proper decoding of at least one of the markings on the surface. In block 126, the location and orientation information of a reference point of the detected view with respect to the coded surface is determined. The reference point associated with the captured image may include, for example, the cross-hairs at the center of the image. Block 128 includes determining the location and orientation information of a reference point of the module with respect to the coded surface. This calculation is made to account for any offset between the reference point of the optical device that senses the image of the surface and a particular reference point of the module. This block may be omitted from the method if the reference point of the captured image is the same as the reference point of the module. Otherwise, when an offset exists, the offset can be established at the time of manufacture or assembly of the module.

In some embodiments, the location and orientation information of the reference point of the module determined in block 128 can be used in a virtual reality system. Block 130 represents an application of this information in virtual reality. For example, the virtual reality system may be a surgical simulation system, such as a laparoscopic simulation system, for allowing a trainee to practice surgical procedures in a virtual realm. In laparoscopic simulation embodiments, for instance, the location and orientation information may be used to represent an initial entry point in which a virtual laparoscopic tool is inserted into a virtual patient.

It should be understood that the steps, processes, or operations described herein may represent any module or code sequence that can be implemented in software or firmware. In this regard, these modules and code sequences can include commands or instructions for executing specific logical steps, processes, or operations within physical components. It should further be understood that one or more of the steps, processes, and/or operations described herein may be executed substantially simultaneously or in a different order than explicitly described, as would be understood by one of ordinary skill in the art.

The embodiments described herein merely represent examples of implementations and are not intended to necessarily limit the present disclosure to any specific embodiments. Instead, various modifications can be made to these embodiments as would be understood by one of ordinary skill in the art. Any such modifications are intended to be included within the spirit and scope of the present disclosure and protected by the following claims

We claim:

1. A system for determining location and orientation of an object, the system comprising:
    an optical device physically supported by the object at a fixed position with respect to a reference point of the object;
        wherein the object is configured to rest on a surface, the surface comprising a reference pattern the reference pattern having a plurality of markings, the plurality markings including encoded information capable of being used to determine a location and orientation of the object; and
        wherein the optical device is configured to be positioned on the object at a predetermined height above the reference pattern and is configured to have a predetermined viewing angle, the predetermined height and predetermined viewing angle configured to allow the optical device to capture an image of a portion of the reference pattern, the optical device further configured to generate and transmit an image signal comprising image data associated with the image; and
    a processing device in communication with the optical device, the processing device configured to receive the image signal from the optical device and to calculate a location and orientation of the reference point based at least in part on the image of the portion of the reference pattern.

2. The system of claim 1, wherein each marking includes a feature that is common to the other markings, and wherein the processing device is further configured to analyze the common feature to determine the orientation information.

3. The system of claim 1, wherein the predetermined height and predetermined viewing angle are configured to allow the optical device to view about one square inch of the surface.

4. The system of claim 1, wherein the array of markings comprises an array of triangles, the length of a first side of each triangle being configured to correlate to a first coordinate value of the surface, and the length of a second side of each triangle being configured to correlate to a second coordinate value of the surface.

5. The system of claim 1, wherein each marking of the array of markings comprises a large figure common to the other markings and a small figure common to the other markings, the positioning of the small figure with respect to the large figure being configured to correlate to coordinate values of the surface.

6. The system of claim 1, wherein the array of markings comprises bar codes that encode coordinate information.

7. The system of claim 1, wherein the object is a module associated with a laparoscopic simulator, and wherein the location information corresponds to an entry point of a virtual laparoscopic tool into a virtual patient.

8. The system of claim 7, wherein the surface corresponds to at least a portion of an abdomen of a dummy patient.

9. The system of claim 8, further comprising a depiction of physical features of a body of a patient applied to the surface.

10. The system of claim 8, further comprising at least a portion of a mannequin representing the body of the dummy patient outside the boundary of the surface.

11. The system of claim 1, wherein the optical device is an image capture device.

12. The system of claim 11, wherein the image capture device comprises a resolution of about 500 pixels by 500 pixels.

13. The system of claim 1, wherein the surface is substantially flat.

14. An object placement analyzing system comprising:
    means for capturing an image of a portion of a surface, the surface including an array of markings visible to the capturing means, the markings including an orientation reference mark and encoded location information, wherein the means for capturing an image is positioned on the object at a predetermined height above the surface and is configured to have a predetermined viewing angle, the predetermined height and predetermined viewing angle being configured to allow optical device to view at least one marking;
    means for analyzing the captured image to calculate location and orientation information of an object with respect to the surface;

wherein the position of the object is associated with the position of the capturing means.

15. The object placement analyzing system of claim 14, wherein the analyzing means comprises means for detecting a reference feature associated with the orientation reference mark.

16. The object placement analyzing system of claim 15, wherein the analyzing means further comprises means for translating and rotating the orientation reference mark to determine translation coordinates and a rotational angle.

17. The object placement analyzing system of claim 16, wherein the analyzing means further comprises means for decoding at least one marking to determine the location information encoded in the marking.

18. The object placement analyzing system of claim 17, wherein the analyzing means further comprises means for calculating coordinates of a reference point of the object with respect to the surface by processing the translation distance, rotational angle, and decoded location information.

19. The object placement analyzing system of claim 14, wherein the location and orientation information is provided to a virtual reality simulator.

20. The object placement analyzing system of claim 19, wherein the virtual reality simulator is a laparoscopic simulator.

21. A method of determining location and orientation, the method comprising:
  instructing a user to position a module on a surface having encoded information related to location information, wherein the module comprises an optical device positioned at a predetermined height above the surface and configured to have a predetermined viewing angle, the predetermined height and predetermined viewing angle being configured to allow optical device to view at least one marking;
  determining location and orientation information associated with the position of a reference point of an image frame with respect to the surface, the image frame comprising a view of at least a portion of the encoded information of the surface; and
  determining location and orientation information associated with the position of a reference point of the module with respect to the surface.

22. The method of claim 21, further comprising:
  receiving an indication from the user when the module is positioned on the encoded surface; and
  in response to receiving the indication, instructing the user to secure the module to the coded surface.

23. The method of claim 21, wherein determining location and orientation information further comprises determining location and orientation based on the location and orientation information associated with the position of the reference point of the image frame and based on a predetermined offset between the reference point of the image frame and the reference point of the module.

24. The method of claim 21, further comprising:
  using the location and orientation information of the reference point of the module in a laparoscopic simulation procedure;
  wherein the reference point of the module corresponds to an entry point of a virtual laparoscopic tool within a virtual patient.

* * * * *